United States Patent
Cowan et al.

(10) Patent No.: US 9,114,215 B2
(45) Date of Patent: Aug. 25, 2015

(54) MULTIPLE COMPARTMENT SYRINGE

(71) Applicant: MEDRAD, INC., Indianola, PA (US)

(72) Inventors: Kevin P. Cowan, Allison Park, PA (US); Edward J. Rhinehart, Monroeville, PA (US); Anthony S. McCoppin, Glenshaw, PA (US); Barry L. Tucker, Verona, PA (US)

(73) Assignee: Bayer Medical Care Inc., Indianola, PA (US)

( * ) Notice: Subject to any disclaimer, the term of this patent is extended or adjusted under 35 U.S.C. 154(b) by 47 days.

(21) Appl. No.: 13/802,372

(22) Filed: Mar. 13, 2013

(65) Prior Publication Data

US 2014/0276039 A1  Sep. 18, 2014

(51) Int. Cl.
*A61M 5/00* (2006.01)
*A61M 5/315* (2006.01)
*A61M 5/19* (2006.01)
*A61M 5/14* (2006.01)
*A61M 5/178* (2006.01)
*A61M 5/31* (2006.01)

(52) U.S. Cl.
CPC ........... *A61M 5/31513* (2013.01); *A61M 5/007* (2013.01); *A61M 5/19* (2013.01); *A61M 5/31596* (2013.01); *A61M 2005/1404* (2013.01); *A61M 2005/1787* (2013.01); *A61M 2005/3103* (2013.01); *A61M 2005/3128* (2013.01); *A61M 2005/3132* (2013.01); *A61M 2005/31598* (2013.01)

(58) Field of Classification Search
CPC ........... A61M 2005/1787; A61M 2005/31598; A61M 2005/1403
USPC .................... 600/432; 604/89, 191
See application file for complete search history.

(56) References Cited

U.S. PATENT DOCUMENTS

| 3,923,058 | A | * | 12/1975 | Weingarten | ................... 604/191 |
| 4,188,949 | A | | 2/1980 | Antoshikiw | |
| 5,489,267 | A | | 2/1996 | Moreno et al. | |
| 5,522,804 | A | * | 6/1996 | Lynn | ............................. 604/191 |
| 5,643,218 | A | | 7/1997 | Lynn et al. | |

(Continued)

FOREIGN PATENT DOCUMENTS

| EP | 2222358 | 1/2013 |
| WO | 2012006555 A1 | 12/2012 |

OTHER PUBLICATIONS

International Search Report and Written Opinion dated Sep. 9, 2014 re PCT/US14/24265.

*Primary Examiner* — Gerald Landry, II
(74) *Attorney, Agent, or Firm* — Joseph L. Kent; David Schramm; James R. Stevenson

(57) ABSTRACT

Various syringe systems are disclosed. One illustrative syringe system may include a syringe body having a hollow lumen and a distal end. The syringe body may be configured to house a plurality of fluids therein. A first plunger may be positioned in the hollow lumen of the syringe body, forming a first seal with an inner wall of the syringe body, and forming a first compartment between the first plunger and the distal end of the syringe. A second plunger may be positioned proximal to the first plunger in the hollow lumen of the syringe body, forming a second seal with the inner wall of the syringe body, and forming a second compartment between the first plunger and the second plunger. A plurality of recesses may be disposed about the inner wall of the syringe body near the distal end of the syringe body.

11 Claims, 9 Drawing Sheets

(56) References Cited

U.S. PATENT DOCUMENTS

| | | |
|---|---|---|
| 5,665,068 A | 9/1997 | Takamura |
| 5,769,824 A | 6/1998 | Hjertman et al. |
| 5,971,953 A * | 10/1999 | Bachynsky .................... 604/90 |
| 7,094,222 B1 * | 8/2006 | Siekas et al. ................. 604/191 |
| 7,632,245 B1 | 12/2009 | Cowan et al. |
| 7,998,106 B2 | 8/2011 | Thorne, Jr. et al. |
| 8,021,343 B2 | 9/2011 | Nalesso et al. |
| 8,529,517 B2 | 9/2013 | Lee |
| 2006/0084909 A1 * | 4/2006 | Tai ................................. 604/85 |
| 2007/0129671 A1 * | 6/2007 | Mu ................................. 604/82 |
| 2008/0082044 A1 | 4/2008 | Sharon et al. |
| 2009/0247985 A1 * | 10/2009 | Melsheimer et al. ......... 604/506 |
| 2010/0082015 A1 * | 4/2010 | Chebator ..................... 604/533 |
| 2010/0228121 A1 | 9/2010 | Kazuhiro et al. |
| 2011/0046602 A1 * | 2/2011 | Grimm et al. ................ 604/506 |
| 2012/0130236 A1 * | 5/2012 | Nystrom ...................... 600/432 |
| 2012/0191041 A1 * | 7/2012 | Pullara ......................... 604/110 |

\* cited by examiner

MULTIPLE COMPARTMENT SYRINGE

BACKGROUND

During a radiological procedure, a contrast medium may be administered to provide improved imaging of anatomical features in a patient. A physician may typically order a specific amount of contrast medium deemed necessary to view these anatomical features. Since the contrast medium may be expensive, it may be important to make sure that the complete dose is administered and that little or no waste is generated. In addition, the contrast medium may need to be pushed to a region of interest or diluted to avoid too much contrast in a region of interest.

Previous attempts to ensure complete contrast medium administration, pushing to a region of interest, and/or dilution involved injecting a flushing material, such as saline solution and/or the like, immediately after the contrast medium in order to flush the administration tube of all residual contrast medium, push the contrast to a region of interest, or dilute the contrast. In some radiological procedures, this may be completed by means of an automated device. However, in some radiological procedures, a manual device may be used for various reasons, such as, for example, an automated device is not available or the procedure does not require the level of delivery control that can be afforded by an automated device. However, the manual device currently used in the art lacks an ability to control delivery in a manner similar to an automated device, thus leading to waste of contrast medium, improperly delivered contrast medium, and/or improperly diluted contrast medium.

Furthermore, it may be necessary to assure that the access vein of the patient remains open when the contrast medium is not actively being delivered. For some patients with diseased vasculature, the vein may collapse when not being actively supplied by contrast medium. In such a condition, some amount of fluid, such as saline solution and/or the like, may be delivered to the vein to keep the vein open ("KVO").

SUMMARY

In an embodiment, a syringe may include a syringe body having a hollow lumen and a distal end, and the syringe body may be configured to house a plurality of fluids therein. A first plunger may be positioned in the hollow lumen of the syringe body, forming a first seal with an inner wall of the syringe body, and forming a first compartment between the first plunger and the distal end of the syringe. A second plunger may be positioned proximal to the first plunger in the hollow lumen of the syringe body, forming a second seal with the inner wall of the syringe body, and forming a second compartment between the first plunger and the second plunger. A plurality of recesses may be disposed about the inner wall of the syringe body near the distal end of the syringe body.

In an embodiment, a syringe system may include a syringe body having a hollow lumen and a distal end comprising a syringe tip, and the syringe body may be configured to house a plurality of fluids therein. Additionally, a first plunger may be positioned in the hollow lumen of the syringe body, forming a first seal with an inner wall of the syringe body, and forming a first compartment between the first plunger and the distal end of the syringe. A second plunger may be positioned proximal to the first plunger in the hollow lumen of the syringe body, forming a second seal with the inner wall of the syringe body, and forming a second compartment between the first plunger and the second plunger. A transfer tube in fluid may be connection with the second compartment and the syringe tip.

In an embodiment, a syringe system may include a syringe body having a hollow lumen and a distal end having a syringe tip. The syringe body may be configured to house a plurality of fluids therein. The syringe system may also include a first plunger positioned in the hollow lumen of the syringe body. The first plunger may form a first seal with an inner wall of the syringe body, and may form a first compartment between the first plunger and the distal end of the syringe. A second plunger may be positioned proximal to the first plunger in the hollow lumen of the syringe body, forming a second seal with the inner wall of the syringe body, and forming a second compartment between the first plunger and the second plunger. The syringe system may also include a transfer tube in fluid connection with the second compartment. The transfer tube may include a valve having an outlet, where the valve is in fluid communication with the syringe tip. The syringe system may also include an outlet port fluidly connected to an outlet of the valve. An orientation of the valve may include one of a first opening state to allow fluid flow from the syringe tip to the outlet port, a second opening state to allow fluid flow from the transfer tube to the outlet port, a third opening state to allow fluid flow from both the syringe tip and the transfer tube to the outlet port, and a closed state to block flow of fluid from the syringe tip and the transfer tube.

In an embodiment, a syringe system may include a syringe body having a hollow lumen and a distal end. The syringe body may be configured to house a plurality of fluids therein. The syringe system may also include a first plunger positioned in the hollow lumen of the syringe body, forming a first seal within an inner wall of the syringe body, and forming a first compartment between the first plunger and the distal end of the syringe, the first plunger comprising a hollow lumen therein. A second plunger may be positioned in the hollow lumen of the first plunger, forming a second seal within an inner wall of the first plunger, and forming a second compartment between the first plunger and the second plunger.

In an embodiment, a syringe system may include a syringe body having a first chamber, a second chamber, and an outlet fluidly connected to the first chamber and the second chamber. The first chamber may be positioned adjacent to the second chamber. The first chamber may have a diameter that is smaller than a diameter of the second chamber. The first chamber may be configured to house a first fluid and the second chamber may be configured to house a second fluid. The syringe system may also include a first plunger positioned in the first chamber and a second plunger positioned in the second chamber. The syringe system may also include an adjustable stop that is configured to stop distal movement of the first plunger after the first plunger has traversed a defined distance. The second plunger may be configured to move in a distal direction to push the second fluid out of the second chamber into an outlet. The first fluid may be drawn out of the first plunger via a Venturi effect upon distal movement of the second plunger.

DETAILED DESCRIPTION

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

For purposes of the description hereinafter, the terms "upper," "lower," "right," "left," "vertical," "horizontal," "top," "bottom," "lateral," "longitudinal," and derivatives thereof shall relate to the orientation of embodiments disclosed in the figures. However, embodiments may assume alternative variations and step sequences, except where expressly specified to the contrary. The specific devices and processes illustrated in the attached drawings and described in the following specification, are exemplary embodiments. Hence, physical characteristics related to the embodiments disclosed herein are not to be considered as limiting.

The word "proximal" refers to a direction relatively closer to a clinician or operator using the device described herein, and the word "distal" refers to a direction relatively further from the clinician or operator. For example, the end of a syringe placed nearest the body of a patient is considered a distal end of the syringe, while the end closes to the clinician is a proximal end of the syringe. The terms "axial" or "axially" refer generally to an axis around which the particular objects being referred to are preferably formed (although not necessarily symmetrically therearound). The term "radial" refers generally to a direction normal to the axis or along a radius of an object having a circular cross-section.

Various embodiments of the present disclosure may be directed to devices and methods of use thereof that use a manual device to deliver a bolus of contrast medium followed by an amount of saline solution. In various embodiments, this may serve to flush the line to ensure all of the contrast is delivered to the patient, to move the contrast to a region of interest, and/or to dilute the contrast concentration. In various embodiments, the devices and methods of use may further be capable of delivering a small amount of fluid to maintain vein patency during contrast medium administration.

Figure 1A:
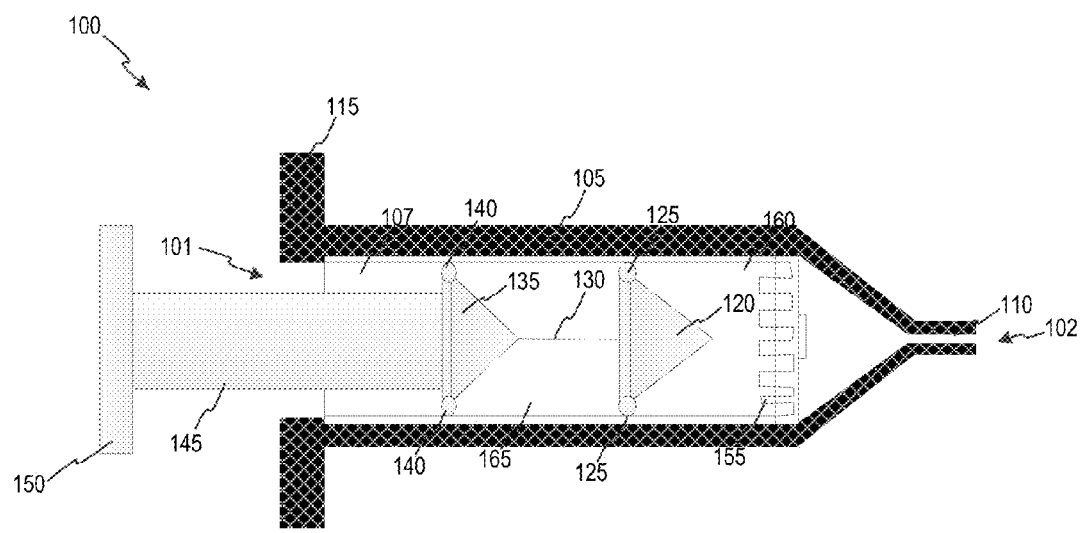
FIGS. 1A-1B depict a side view of a syringe according to an embodiment.

FIG. 1A depicts a side view of a syringe, generally designated 100, according to an embodiment. The syringe 100 may generally include a syringe body 105 having a hollow lumen 107, a proximal end 101, and a distal end 102 having a tip 110. The syringe body 105 is not limited in shape or size by this disclosure, and may be any shape or size, particularly shapes and sizes of syringe bodies commonly known by those skilled in the art. In various embodiments, the syringe body 105 may substantially cylindrical. In various embodiments where the syringe 100 is configured for use in computed tomography (CT) applications and the like, the syringe body 105 may be configured to contain about 20 ml to about 150 ml of fluid therein. In particular embodiments, the syringe body may be configured to contain about 20 ml, about 25 ml, about 30 ml, about 50 ml, about 75 ml, about 100 ml, about 125 ml, about 150 ml, or any value or range between any two of these values. In various embodiments where the syringe 100 is configured for use in magnetic resonance (MR) applications and the like, the syringe body 105 may be configured to contain about 5 ml to about 20 ml of fluid therein. In particular embodiments, the syringe body may be configured to contain about 5 ml, about 10 ml, about 12.5 ml, about 15 ml, about 20 ml, or any value or range between any two of these values.

In various embodiments, the hollow lumen 107 may include a plurality of plungers disposed therein. For example, in the present embodiment, the hollow lumen 107 may have a first plunger 120 and a second plunger 135. However, those skilled in the art will recognize that more than two plungers may be used without departing from the scope of this disclosure. In various embodiments, the first plunger 120 may form a seal against the interior of the syringe body 105 by means of a first seal 125. In some embodiments, the first seal 125 may be a separate component from the first plunger 120, such as, for example, an added O-ring and/or the like. In these embodiments, the first seal 125 may be fixedly attached to the first plunger 120 by any means of attachment, including attachment apparatuses, adhesives, and/or the like, or the first seal may be removably attached to the first plunger. In other embodiments, the first seal 125 may be fabricated as a portion of the first plunger 120. Similarly, in various embodiments, the second plunger 135 may form a seal against the interior of the syringe body 105 by means of a second seal 140. In some embodiments, the second seal 140 may be a separate component from the second plunger 135, such as, for example, an added O-ring and/or the like. In these embodiments, the second seal 140 may be fixedly attached to the second plunger 135 by any means of attachment, including attachment apparatuses, adhesives, and/or the like, or the second seal may be removably attached to the second plunger. In other embodiments, the second seal 140 may be fabricated as a portion of the second plunger 135. The first plunger 120, the second plunger 135, the first seal 125, and the second seal 140 may each be made of any material now known or later developed that is known by those skilled in the art for use in plungers and/or seals. Specific examples may include polymers, rubber, and/or the like.

In various embodiments, a first compartment 160 may be formed between the first plunger 120 and the distal end 102 of the syringe body 105. The first compartment 160 may be configured to contain a fluid therein. In particular embodiments, the fluid may include a contrast medium. In various embodiments, a second compartment 165 may be formed between the second plunger 135 and the first plunger 120. The second compartment 165 may also be configured to contain a fluid therein. In particular embodiments, the fluid may include a flushing fluid. One such specific example of a flushing fluid may be saline. The volume of the first compartment 160 may be determined by the distance between the first plunger 120 and the distal end 102 of the syringe body 105, as well as the circumference of the syringe body. The volume of the second compartment 165 may be determined by the distance between the first plunger 120 and the second plunger 135, as well as the circumference of the syringe body 105.

In various embodiments, the first plunger 120 and the second plunger 135 may be joined together by means of a connection piece 130. The connection piece 130 may be constructed so that when force is applied on the second plunger 135, some of the force is transferred to the first plunger 120 to effect movement of the first plunger along with the second plunger. In some embodiments, movement may be bidirectional, i.e., the force can be directed proximally or distally to move the first plunger 120 and the second plunger 135 in either a proximal or distal direction within the syringe. In these embodiments, the connection piece 130 may be constructed of a rigid material that does not bend or collapse when pressure is applied to it. The connection piece 130 may further be constructed of any material that does not impact any fluid that may come into contact with it. In other embodiments, movement may be unidirectional, i.e., a force that pushes the second plunger 135 in a distal direction may not be transferred to the first plunger 120 so that the first plunger stays in place, but when the opposite force in a proximal direction is placed on the second plunger, the force is transferred to the first plunger, causing it to move as well. In some embodiments, as shown in FIG. 1A, this unidirectional movement may be possible by using a connection piece 130' that is constructed of a collapsible material. Specific examples of collapsible materials may include filaments, monofilaments, fibers, polymers, and the like. In some embodiments, the connection piece 130 (or 130') may include one or more magnets so that the force on the second plunger 135 causes a force on the first plunger 120 due to magnetic attraction. In some embodiments, the connection piece 130 (or 130') may include a releasable pin or similar locking device that can lock or unlock the connection piece to effectuate a desired movement of the plungers 120, 135 as described herein. As in the other constructions, the connection piece 130 (or 130') may further be constructed of any material that does not impact any fluid that may come into contact with it.

In various embodiments, particularly embodiments in which the connection piece is a collapsible material 130', the first plunger 120 may be moved towards the distal end 102 of the syringe body 105 under force from the fluid located within the second chamber 165. For example, due to the actions of the second seal 140 and the first seal 125, the fluid contained within the second compartment 165 does not leak or compress, but rather acts as a hydraulic lock, thereby transferring force from the second plunger 135 to the first plunger 120. In this manner, the fluid located in the first compartment 160 may be pushed distally by the first plunger 120, where, in some embodiments, it may be forced out the syringe tip 110.

In various embodiments, the second plunger 135 may be connected to a piston 145 that may at least partially extend out of an opening in the proximal end 101 of the syringe body 105. The second plunger 135 may be attached to the piston 145 by any means of attachment, including, but not limited to, any number of clips, fasteners, hooks, adhesives, and/or the like. In some embodiments, the second plunger 135 may be molded as a portion of the piston 145. In some embodiments, the piston 145 may have a thumb piece 150 proximally attached thereto. The thumb piece 150 may generally provide a stable surface to allow the user of the syringe 100 to push and/or pull the piston 145, and correspondingly the second plunger 135 and/or the first plunger 120. The thumb piece 150 depicted herein is a generally flat surface; however, those skilled in the art will recognize that the shape and size of the thumb piece is not limited by this disclosure, and may include any number of rings, openings, contoured surfaces, and/or the like without departing from the scope of the present disclosure. Persons skilled in the art will also note that the term 'thumb piece' is not to be limiting; the user may use any object to manipulate the thumb piece 150 as described herein.

In various embodiments, the interior surface of the syringe body 105 may include a plurality of recesses 155 disposed therein, causing a void in portions of the interior surface at the location of each recess. In some embodiments, the plurality of recesses 155 may be disposed about the inner wall of the syringe body 105 near the distal end 102. The shape and size of the recesses 155 is not limited by this disclosure, and may generally be any shape and/or size that will break the seal between the syringe body 105 and the first seal 125 of the first plunger 120. In some embodiments, the recesses 155 may be scalloped. In other embodiments, the recesses 155 may be crenelated. The recesses 155 may be located at any position on the inside wall of the syringe body 105, and may be positioned so as to correspond to an amount of fluid that is desired in the first compartment 160 and/or the second compartment 165. However, the recesses 155 cannot be located so far distal in the syringe body that the first seal 125 does not contact it, as the fluid in the second compartment 165 would not be released. In some embodiments, the recesses 155 may be positioned at a tapered transition point from the cylindrical syringe body 105 to the tip 110.

In various embodiments, one or more finger guards 115 may be positioned at a location that is generally located at or near the proximal end 101 of the syringe body 105. In some embodiments, the finger guards 115 may generally be located on an outside surface of the syringe body 105 and may generally extend from the outside surface of the syringe body. In some embodiments, the finger guards 115 may act to provide stability to the syringe 100 during operation. In some embodiments, a user may use the finger guards 115 to prevent movement of the syringe 100 during operation. In some embodiments, the user may use the finger guards 115 to prevent the syringe 100 from slipping out of the user's hand. In some embodiments, the user may use the finger guards 115 to protect the user's fingers. In some embodiments, the finger guards 115 may act as a stopping device to prevent the piston 145 from moving further distally inside the syringe body 105. The shape and size of the finger guards 115 are not limited by this disclosure, and may be any shape and/or size known in the art. Specific examples of shapes may be ring shaped, wedge shaped, T-shaped, curved, curved with finger indentations, and/or the like.

Figure 1B:
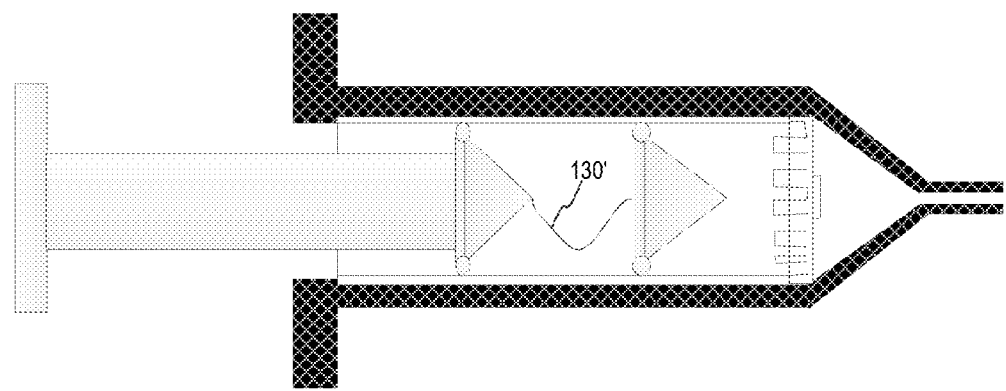
Figure 2A:
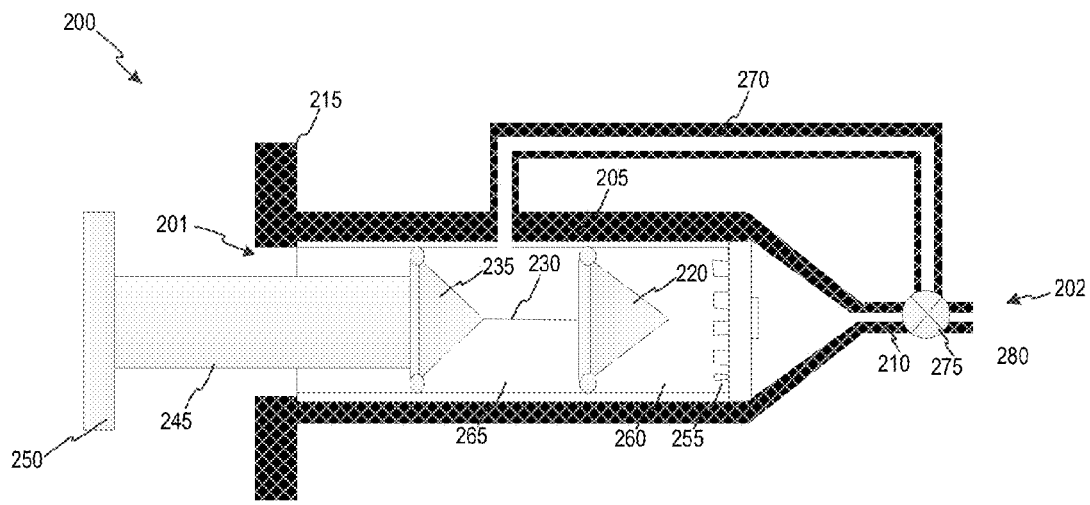
FIG. 2A depicts a side view of an alternative syringe having a transfer tube according to an embodiment.

FIG. 2A depicts a side view of an alternative syringe, generally designated 200, according to an embodiment. Similar to the syringe 100 disclosed with respect to FIGS. 1A and 1B above, the syringe 200 may include a syringe body 205 having a proximal end 201 and a distal end 202. The syringe body 205 may have a first plunger 220 and a second plunger 235 disposed within it. The first plunger 220, the second plunger 235, and a tip 210 may define a first compartment 260 and a second compartment 265 therein for storing two different types of fluid, as previously described herein. The first plunger 220 and the second plunger 235 may be moved within the syringe body 205 by applying a force to the thumb piece 250 portion of a piston 245, as previously described herein. In some embodiments, movement of the first plunger 220 may be aided by the connection piece 230, as described herein. In alternate embodiments, movement of the first plunger 220 may be aided by transfer of force on the second plunger 235 to the first plunger 220 via a fluid located in the second compartment 265, as also described herein.

In various embodiments, the alternative syringe of FIG. 2A may differ from the syringe of FIGS. 1A and 1B by including, among other things, a transfer tube 270, a valve 275, and one or more outlet ports 280. In some embodiments, the recesses 255 may not be present. In some embodiments, the functions of these additional elements, as described herein, may allow for the syringe 200 to provide a "keep vein open" (KVO) function. The KVO function may be used during a long term injection procedure to ensure that access to a vein remains available for fluid injection and does not collapse when fluid is not being administered. In some embodiments, the functions of these additional elements may allow for the syringe 200 to provide functionality for delivering the fluid of the second compartment 265 before delivering the fluid of the first compartment 260 and vice versa. In some embodiments, the functions of these additional elements may allow for the syringe 200 to provide functionality for mixing at least a portion of the contents in the first compartment 260 with at least a portion of the contents in the second compartment 265 during delivery to a patient. In some embodiments, the functions of these additional elements may allow for the syringe 200 to be in an "off" state, thus preventing the contents from either compartment 260, 265 from escaping, such as to prevent leakage when the syringe is not in use.

In various embodiments, the transfer tube 270 may be in fluid connection with the contents of the second compartment 265 within the syringe body 205. Thus, in some embodiments, the syringe body 205 may contain an opening and/or a bore therein for attachment of the transfer tube 270 to allow for a fluid connection thereof. The construction of the transfer tube 270 is not limited by this disclosure any may be of any shape, size, and/or composition. In some embodiments, the transfer tube 270 may be generally hollow to allow transfer of a fluid therethrough, and may generally be made of a substance that does not impact the fluid flowing therethrough.

Figure 2B:
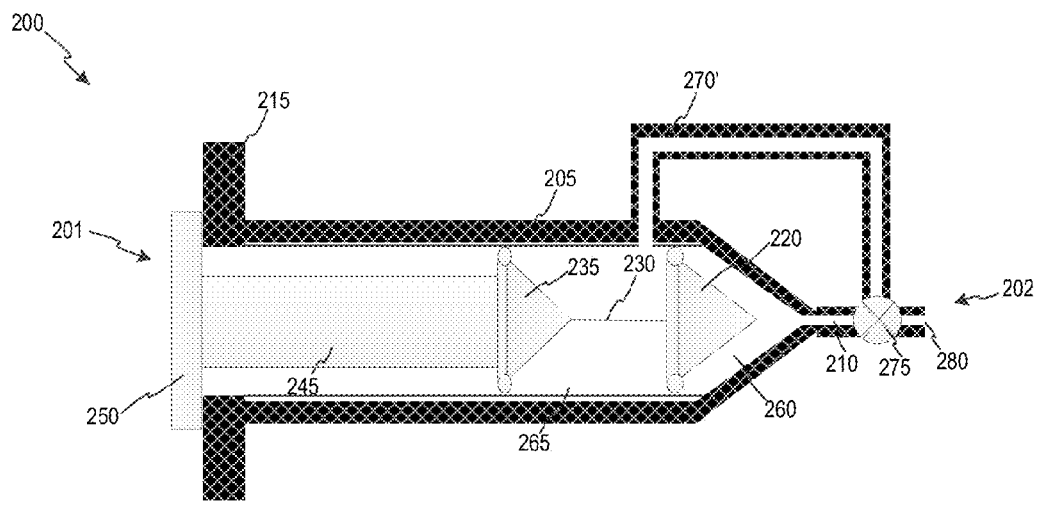
FIG. 2B depicts a side view of the alternative syringe of FIG. 2A with an alternatively positioned transfer tube according to an embodiment.

In alternative embodiments, such as the embodiment shown in FIG. 2B, the transfer tube 270' may be in fluid connection with the contents of both the first compartment 260 and the second compartment 265, depending on the positioning of the plungers 220, 235. In some embodiments, the transfer tube 270' may act as an alternative to the recesses 255 (FIG. 2A). Thus, the transfer tube 270' may allow for transfer of fluid to/from the first compartment 260 only when first compartment is exposed to the transfer tube and the valve 275 is particularly positioned, as described in greater detail herein. Furthermore, the transfer tube 270' may allow for transfer of fluid to/from the second compartment 265 only when the second compartment is exposed to the transfer tube and the valve 275 is particularly positioned, as described herein. In addition, because the recesses are not present in this embodiment, the first plunger 220 may continue to form a seal with the inner wall of the syringe body 205, even as it is being forced in a distal direction, so fluids in the second compartment 265 will only be able to exit the syringe 200 via the transfer tube 270' when the valve 275 is particularly positioned, as described herein.

Figure 3:
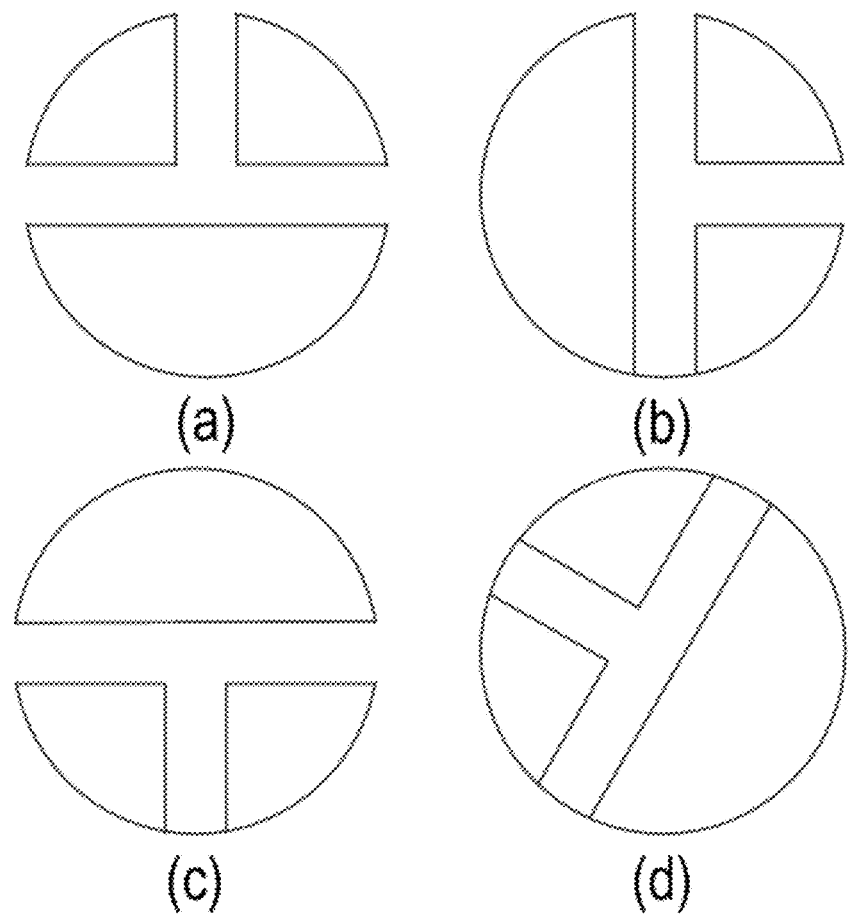
FIG. 3 depicts various alternative orientations of a valve used in the syringe of FIGS. 2A and 2B according to an embodiment.

As shown in either embodiment of FIGS. 2A and 2B, the transfer tube 270 may terminate in the valve 275. In some embodiments, the valve 275 may be in fluid connection with the transfer tube 270, the tip 210 and the outlet port 280. In various embodiments, the valve 275 may be configured to be positioned in one of a plurality of states, in which it is open to any or none of the elements in which it is fluidly connected, as shown in FIG. 3. A first state, as depicted in position (a), allows contents to flow from both the tip 210 and the transfer tube 270 to the outlet port 280. A second state, as depicted in position (b), only allows contents from the transfer tube 270 to be dispensed into the outlet port 280, as it blocks the contents in the tip 210. A third state, as depicted in position (c), only allows contents from the tip 210 to be dispensed into the outlet port 280, as it blocks the contents in the transfer tube 270. A fourth state, as depicted in position (d), does not allow the contents of either location to be dispensed into the outlet port 280 because the valve 275 is closed off to both the transfer tube 270 and the tip 210. Those skilled in the art will recognize that contents may be drawn into the syringe 200 in a similar manner, as described in greater detail herein.

In various embodiments, the outlet port 280 may be configured to receive the contents from the first chamber 260, the second chamber 265, both chambers, or neither chamber depending on the orientation of the valve 275 and/or the location of the transfer tube 270 (or 270'). The outlet port 280 may further be configured to output any contents received to a patient. In some embodiments, the outlet port 280 may be configured to securely attach to additional elements, such as tubes, needles, nozzles, valves, catheters, and the like to aid in delivery of the contents to the patient.

Figure 4:
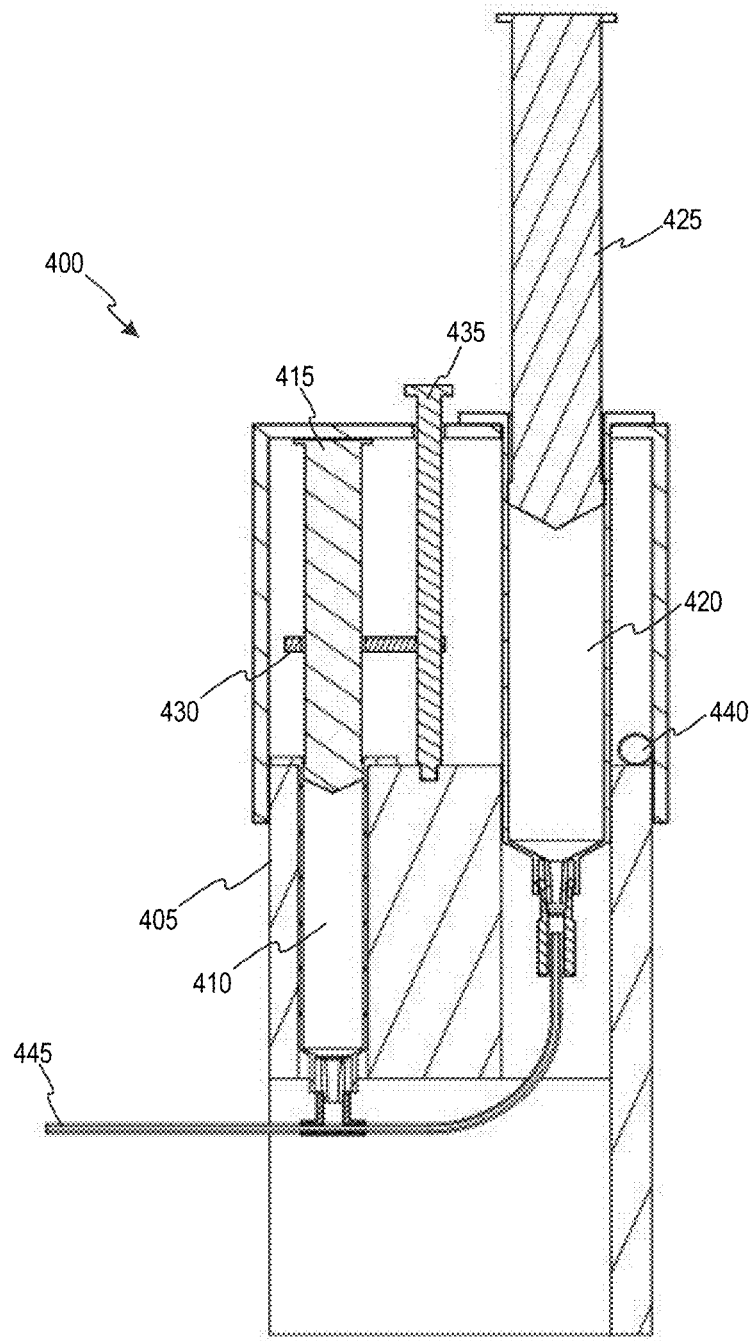
FIG. 4 depicts a side view of another alternative syringe according to an embodiment.

FIG. 4 depicts a side view of another alternative syringe system according to an embodiment. The syringe system 400 may include a syringe body 405 having a first chamber 410 and a second chamber 420. Unlike in other embodiments depicted herein, the first chamber 410 and second chamber 420 may not be in line with each other. Rather, the chambers 410, 420 may be positioned adjacent to each other, such as, for example, substantially parallel to each other. A distal end of each chamber 410, 420 may be fluidly connected to an output 445. In some embodiments, the output 445 may be configured to transmit the contents of the first chamber 410 and/or the second chamber 420 to a subject. In some embodiments, the output 445 may be configured to attach to other devices, such as, for example, tubes, nozzles, needles, valves, catheters, and the like, as described in greater detail herein.

In various embodiments, the first chamber 410 may have a first plunger 415 and a cavity for housing and dispensing a first fluid therein. Similarly, the second chamber 420 may have a second plunger 425 and a cavity for housing and dispensing a second fluid therein. In some embodiments, a diameter of the first chamber 410 may be smaller than a diameter of the second chamber. The second plunger 425 may be actuated by receiving a force in a distal direction, as described in greater detail herein. Because the diameter of the second chamber 420 is larger than the diameter of the first chamber 410, the force on the second plunger 425 that causes fluid to move out of the second chamber and into the output 445 may cause a Venturi effect on the fluid in the first chamber, causing it to be drawn out into the output with the fluid from the second chamber. In some embodiments, a constant force spring 440 may be configured to ensure that the force applied to the second plunger 425 is fluid and uniform to effectuate a smooth delivery of the contents of the chambers 410, 420 to a subject.

In various embodiments, the syringe system 400 may include a stop 430. In some embodiments, the stop 430 may be configured to block movement of the first plunger 415 after movement over a certain distance has occurred. The position of the stop 430 may be adjustable by actuating a stop adjustment screw 435. By changing the positioning of the stop 430, a user can dictate the amount of distance that the first plunger 415 can be moved before being stopped by the stop. In an illustrative example, a force may be applied to the second plunger 425 to cause the first plunger 415 and the second plunger to move distally in their respective chambers 410, 420, as described herein. Once the first plunger 415 reaches the stop 430, additional distal movement of the first plunger may cease, thereby preventing additional fluid from exiting the first chamber 410, while additional distal movement of the second plunger 425 may continue until all of the contents of the second chamber 420 have been displaced out of the second chamber.

Figure 5:
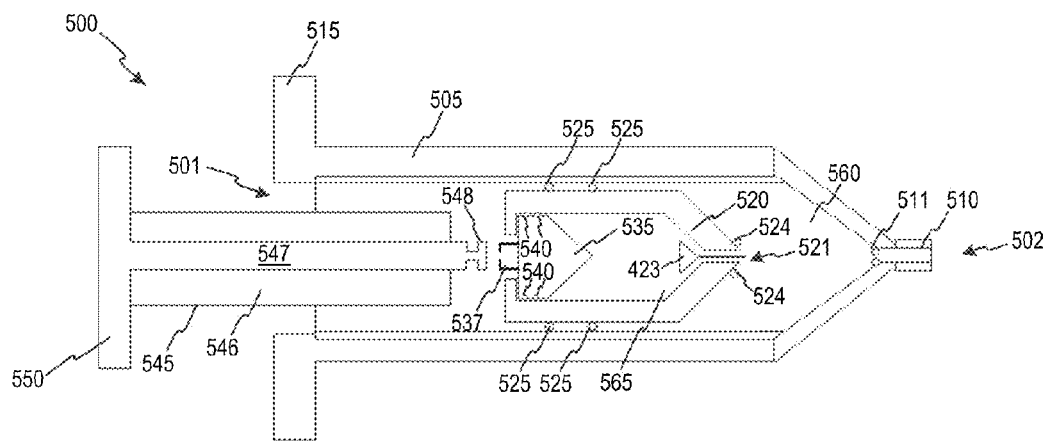
FIG. 5 depicts a side view of yet another alternative syringe according to an embodiment.

FIG. 5 depicts a side view of yet another alternative syringe according to an embodiment. Similar to the syringe 100 disclosed with respect to FIGS. 1A and 1B above, the syringe 500 may include a syringe body 505 having a proximal end 501 and a distal end 502. The syringe body 505 may have a first plunger 520 and a second plunger 535 disposed within it, however, unlike the embodiments of FIGS. 1A and 1B, the second plunger may be located inside the first plunger, as will be described in greater detail herein. The first plunger 520 and the second plunger 535 may be moved within the syringe body 505 by applying a force to the thumb piece 550 portion of a piston 545, as previously described herein.

In various embodiments, the first plunger 520 may form a seal against the interior of the syringe body 505 by means of the first seal 525, as previously described herein. A first chamber 560 may be defined by the first plunger 520 and the tip 510, as previously described herein. The first chamber 560 may further be configured to house a fluid therein, where the fluid is forced out of the tip 510 upon a force applied to the thumb piece 550, as previously described herein.

In various embodiments, the first plunger 520 may be substantially hollow and configured to house at least the second plunger 535 and a check valve 523, such as a one-way check valve or the like, therein. In some embodiments, the second plunger 535 may form a seal against the interior of the first plunger 520 by means of the second seal 540. Accordingly, the second chamber 565 may be defined by the second plunger 535 and the remainder of the hollow space within the first plunger 520. Furthermore, the second plunger 535 may be configured to slidably move within the first plunger 520 independently of movement of the first plunger within the syringe body 505. In some embodiments, the check valve 523 may be configured to activate, thereby plugging an opening in a distal portion 521 of the first plunger 520. In some embodiments, the check valve 523 may further be configured to release, thereby allowing the contents of the second chamber 565 to be released distally into the first chamber 560 and/or the tip 510. In some embodiments, a third seal 524 positioned distally on the first plunger 520 may allow a distal portion of the first plunger to seal against a distal portion of the syringe body 505 so that the fluid from the second compartment 565 does not flow back into the syringe body when it is ejected, as described in greater detail herein.

In various embodiments, the second plunger 535 may be removably attached to at least a portion of the piston 545. In some embodiments, the second plunger 535 may include a proximally located attachment member 537 affixed thereto. The attachment member 537 of the second plunger 535 may generally be configured to removably attach to an attachment member 548 of the piston 545.

In various embodiments, the piston 545 may include at least an inner piston 547 and an outer sleeve 546. In some embodiments, the inner piston 547 may extend from the thumb piece 550 to the attachment member 548. In various embodiments, the inner piston 547 may have a shape and size that, when the inner piston is actuated, it can move independently of the outer sleeve 546, cause the attachment member 548 to attach to the attachment member 537 of the second plunger 535 without substantially contacting the first plunger 520, and force the second plunger to move within the first plunger without causing movement of the first plunger within the syringe body 505. In some embodiments, the outer sleeve 546 can be actuated independently of the inner piston 547 and can further move independently of the inner piston. In some embodiments, the outer sleeve 546 may have a shape and/or size that is configured to allow the outer sleeve to contact at least a portion of the proximal end of the first plunger 520 without substantially contacting the second plunger 535. In some embodiments, a force may be applied to the outer sleeve 546 to cause the outer sleeve to force the first plunger 520 to move within the syringe body 505, as described in greater detail herein. In some embodiments, the inner piston 546 and the outer sleeve 545 may be locked together with a locking mechanism (not shown) so that, when a force is applied to the thumb piece 550, the entire piston 545 moves as one.

In various embodiments, the syringe body 505 may further include one or more valve actuators 511 positioned at a location within the inside surface of the syringe body. In the present example, the valve actuators 511 are located near the tip 510; however, those skilled in the art will recognize that the valve actuators may be positioned at any location without departing from the scope of the present disclosure. In some embodiments, the valve actuators 511 may be configured to release the one-way check valve 521 upon contact between the valve actuators and the check valve. In some embodiments, the valve actuators 511 may be configured to activate the check valve 521 upon removal of contact between the valve actuators and the check valve.

Figure 6A:
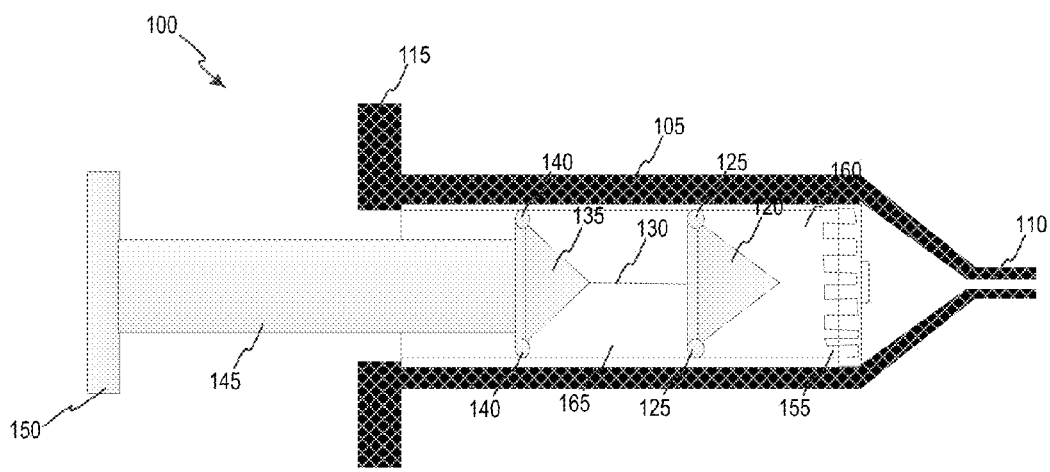
FIGS. 6A-6D depict movement of the various components of the syringe depicted in FIGS. 1A and 1B according to an embodiment.
Figure 6B:
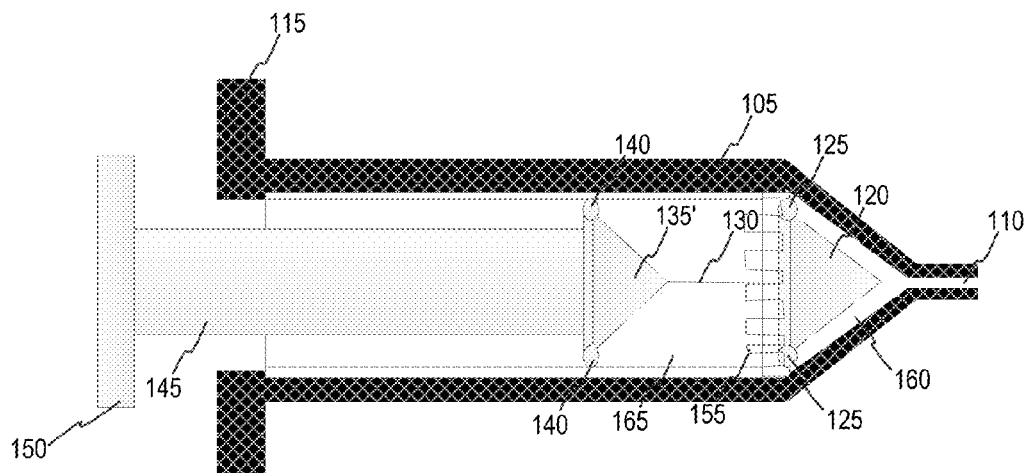

FIGS. 6A-6D depict movement of the various components of the syringe 100 depicted in FIGS. 1A and 1B according to an embodiment. More particularly, FIG. 6A depicts an initial state of the syringe 100 when it is loaded with a first fluid in the first compartment 160 and a second fluid in the second compartment 165. As previously described herein, a user may apply a force on the thumb piece 150 to force the piston 145 in a distal direction into the syringe body 105. As a result, the piston 145 may mechanically force the second plunger 135 in the distal direction towards the syringe tip 110. As previously described herein, due to the actions of the second seal 140 and the first seal 125, the fluid located in the second compartment 165 may not leak or compress, but rather may act as a hydraulic lock, thereby transferring the force from the second plunger 135 to the first plunger 120, causing the first plunger to also move in the distal direction towards the syringe tip 110, as shown in FIG. 6B. Accordingly, the fluid contained in the first compartment 160 may be forced out of the syringe tip 110.

Figure 6C:
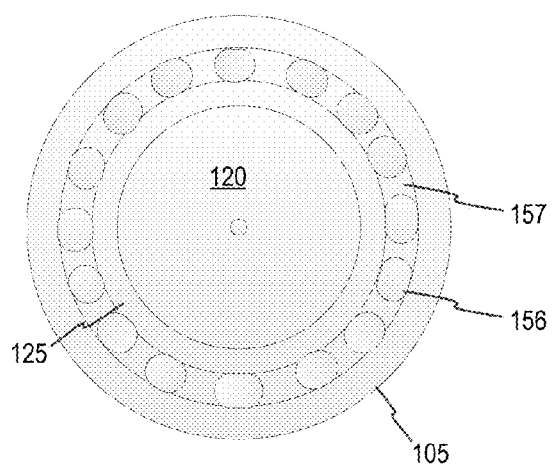

In various embodiments, the fluid located in the first compartment 160 may be pushed out through the tip 110 by the first plunger 120 until the mechanical force on the piston 145 (via the second plunger 135 and the force from the fluid in the second compartment 165) drives the first plunger to the recesses 155. In some embodiments, at the recesses 155, the first seal 125 may no longer act as a fluid seal against the inner surface of the syringe body 105. Because the hydraulic seal of the first plunger 120 against the interior of the syringe body 105 is broken in this state, the fluid located in the second compartment 165 may flow around the recesses 155, through the remaining space in the first compartment 160, and out the tip 110. FIG. 6C depicts a cross sectional view of the syringe 100 as the first seal 125 contacts the recesses 155 according to various embodiments. In some embodiments, the first seal 125 may contact one or more cops 156, but does not fill one or more crenels 157 of the recesses 155. Thus, in some embodiments, the fluid from the second compartment 165 (FIG. 6B) may flow through the crenels 157 and out the tip 110 (FIG. 6B).

Figure 6D:
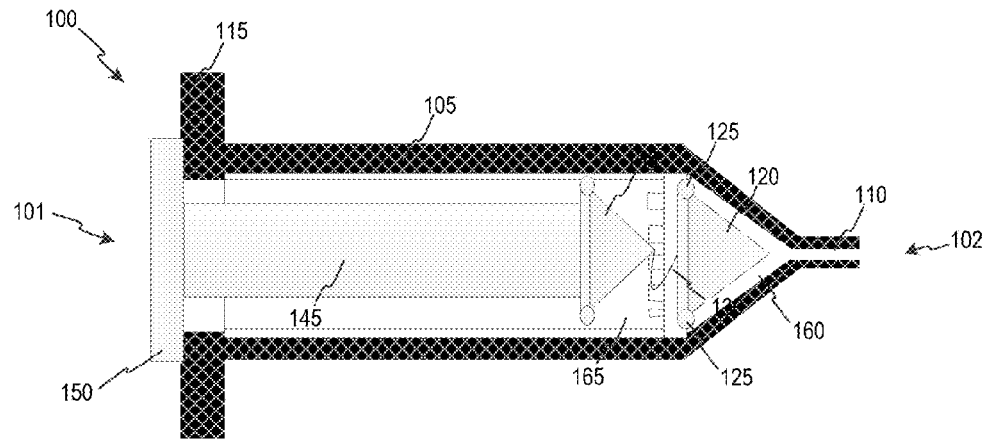

FIG. 6D depicts the result of the completed delivery by the syringe 100 of the fluid from both the first compartment 160 and the second compartment 165 according to various embodiments. In some embodiments, the thumb piece 150 may have been pushed completely to the end of the finger guards 115. As a result, the piston 145 may have moved the length of its travel, and the second plunger 135 may be extended to its most distal position. In some embodiments, the second compartment 165 may have been compressed to a minimum volume, and the fluid previously contained therein may have been delivered around the first plunger 120 and through the first compartment 160, as disclosed in greater detail herein. Although FIG. 6D illustrates a residual volume in the second compartment 165 due to the illustrated geometry of the first plunger 120 and the second plunger 135, it may be appreciated that the two plungers may be fabricated so that the distal surface of the second plunger and the proximal surface of the first plunger allow for a minimal to zero volume when the second plunger is completely extended distally. FIG. 6D also illustrates that the connection piece 130 may be in an un-tensioned state at the end of fluid delivery. As previously described herein, the connection piece 130 may be designed to impart a force on the first plunger 120 when the second plunger 135 is withdrawn towards the proximal end 101 of the syringe body 105, and may not transfer a force to the first plunger while the second plunger is pushed toward the distal end of the syringe.

In various embodiments, the syringe 100 may be filled by operating in a reverse order of delivery. Thus, in some embodiments, an empty syringe 100 may begin with both the first plunger 120 and the second plunger 135 at the distal end 102 of the syringe 105. In some embodiments, the second fluid may be introduced first into the second compartment 165 from the tip 110 when a user moves the thumb piece 150 in a proximal motion away from the finger guard 115. The proximal movement of the thumb piece 150 may cause the piston 145 and the mechanically coupled second plunger 135 to also move proximally. In some embodiments, the second plunger 135 may be withdrawn proximally into the syringe body 105, thereby taking up the slack in the connection piece 130. Once the second plunger 135 has moved sufficiently in a proximal direction into the syringe body 105 (see FIG. 6B), the connection piece 130 may be pulled taut and further proximal motion on the piston 145 may be transferred to the first plunger 120. Once the first seal 125 is pulled into the syringe body 105 proximal to the recesses 155, the second compartment 165 may be sealed, and no additional fluid may be introduced into the second compartment. At this point, the thumb piece 150 may be further retracted proximally. Once the first seal 125 of the first plunger 120 is engaged against the interior surface of the syringe barrel 105, a first fluid introduced through the tip 110 may be delivered to the first compartment 160.

Figure 7A:
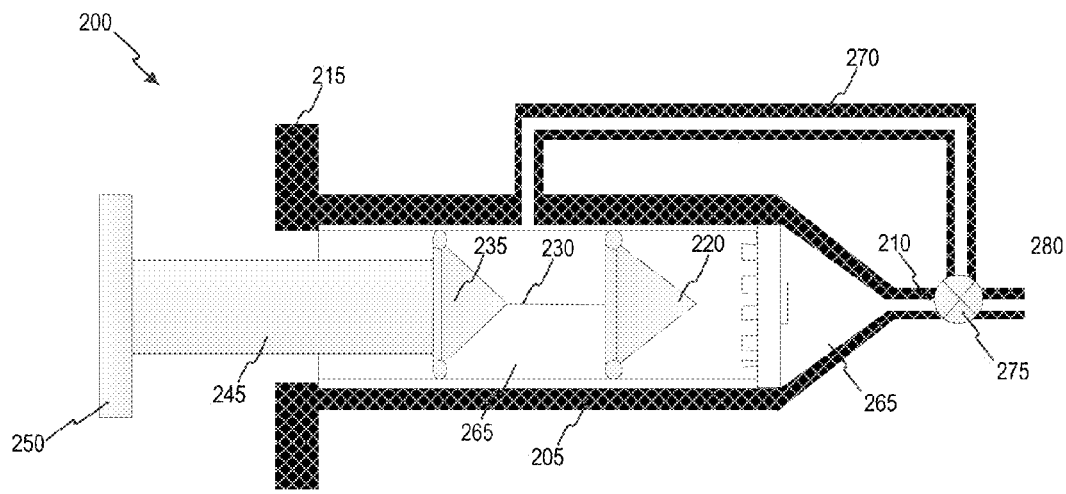
FIGS. 7A-7C depict movement of the various components of the syringe depicted in FIG. 2A according to an embodiment.
Figure 7B:
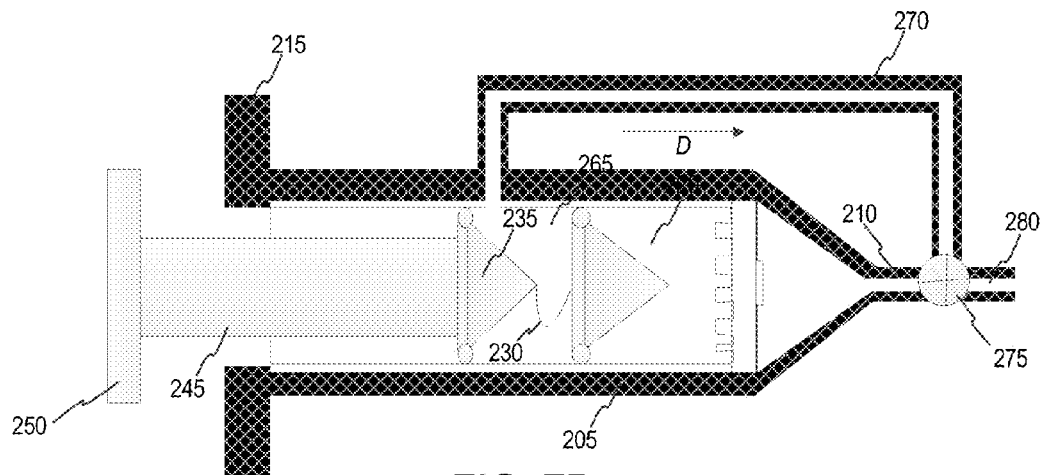
Figure 7C:
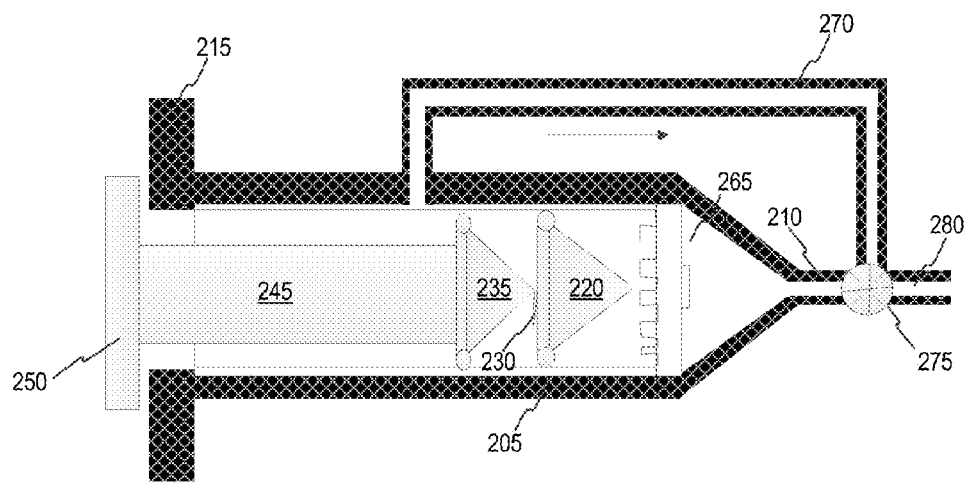

FIGS. 7A-7C depict movement of the various components of the syringe 200 depicted in FIG. 2A according to an embodiment. As described in greater detail herein, pressure on the thumb piece 250 may be transferred through the piston 245 to the second plunger 235. Barring any fluid path from the second compartment 265, a hydraulic lock will force the first plunger 220 in the distal direction, as described in greater detail herein. Thus, if the valve 275 is in either the third or fourth states as shown in FIG. 3, no fluid may flow through the transfer tube 270 from the second compartment and in some embodiments, particularly if the valve 275 is in the third state, fluid from the first compartment 260 will be delivered through the tip 210 and the outlet port 280 in a similar manner as the embodiment shown in FIGS. 1A and 1B. FIG. 7B illustrates the result of the valve 275 in a second state. In some embodiments, when the valve 275 is in either the first or second states (FIG. 3), fluid from the second compartment 265 may travel through the transfer tube 270 as indicated by the directional arrow D and out the outlet port 280. As a result, the hydraulic lock between the second plunger 235 and the first plunger 220 may be released, and the first plunger is no longer driven by the second plunger until they come in physical contact with each other, as shown in FIG. 7C. In some embodiments, because the second plunger 235 can move independently of the first plunger 220, the connection piece 230 may lose tension, as illustrated in FIGS. 7B and 7C.

In various embodiments, it may be appreciated that the syringe 200 may be filled by operating in a reverse order of the delivery, as previously described herein. The valve 275 may be adjusted according to whether it is desired to fill the first compartment 220 or the second compartment 235, and the plungers may be forced in a proximal direction to effect intake of fluid into the respective compartments.

Figure 8A:
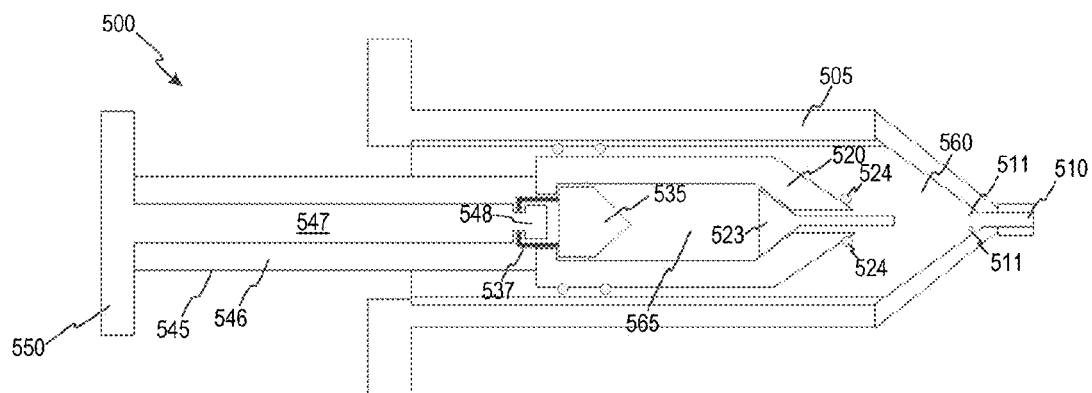
FIGS. 8A-8C depict movement of the various components of the syringe depicted in FIG. 5 according to an embodiment.
Figure 8B:
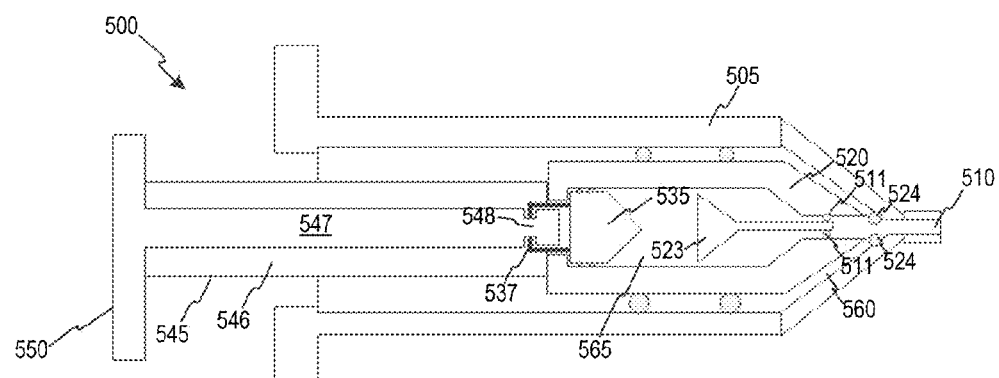
Figure 8C:
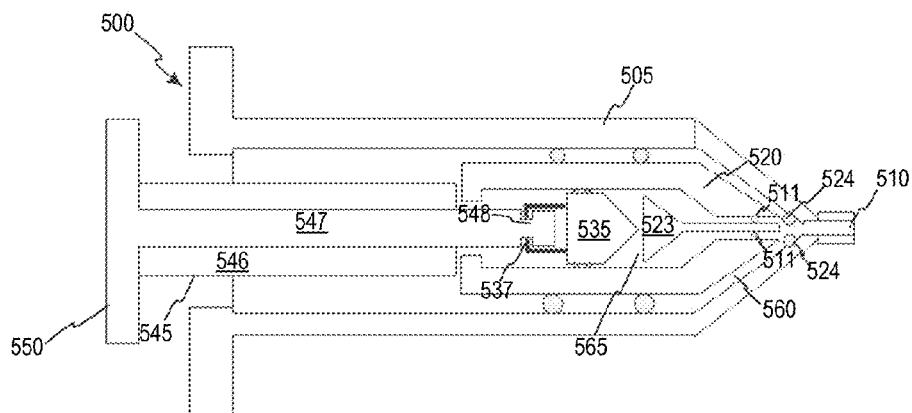

FIGS. 8A-8C depict movement of the various components of the syringe 500 depicted in FIG. 5 according to various embodiments. In some embodiments, the inner piston 547 may be released from the outer sleeve 546 to slide distally, bring the attachment member 548 of the piston in contact with the attachment member 537 of the second plunger 535 and lock the two attachment members together. The inner piston 547 may be locked to the outer sleeve 546 so that they are configured to move in unison and, upon receipt of a force on the thumb piece 550, cause the first plunger 520 to move in a substantially distal direction toward the tip 510. The movement of the first plunger 520 may cause fluid contained within the first compartment 560 to be ejected from the tip 510.

In various embodiments, once the first plunger 520 comes into contact with a distal portion of the syringe body 505, it may form a third seal 524 with the distal portion of the syringe body to prevent fluid in the second compartment 565 from escaping in a proximal direction around the outside of the first plunger. In some embodiments, the valve actuators 511 may apply a force upon contacting the check valve 523, causing the check valve to actuate. In particular embodiments, the valve actuators 511 may apply the force in a proximal direction, thus forcing the check valve 523 to actuate by moving the check valve proximally into the second compartment 565. By forcing the check valve into the second compartment 565, a passageway may open between the second compartment 565 and the tip 510, thus allowing fluid from the second compartment to flow to the tip. In various embodiments, the inner piston 547 may once again be unlocked from the outer sleeve 546 so that it can move independently of the outer sleeve. A force may be applied to the inner piston 547 to cause the second plunger 535 to move in a distal direction within the first plunger 520, thereby forcing the fluid out of the second compartment 565 and through the tip 510.

In various embodiments, it may be appreciated that the syringe 500 may be filled by operating in a reverse order of the delivery, as previously described herein. The second plunger 535 may be forced in a proximal direction by the inner piston 547, thereby drawing fluid into the second compartment 565. Once the second plunger 535 contacts a proximal portion of the first plunger 520, the proximally directed force may draw the first plunger in a proximal direction as well. Removal of the first plunger 520 from the distal portion of the syringe body 505 may cause the valve actuators 511 to allow the check valve 523 to slide distally within the first plunger, thereby sealing the contents of the second compartment 565 therein. Further force upon the first plunger 520 in a proximal direction may allow fluid to be drawn into the first compartment 560, as previously described herein.

Although various embodiments have been described in detail for the purpose of illustration, it is to be understood that such detail is solely for that purpose and that the disclosure is not limited to the disclosed embodiments, but, on the contrary, is intended to cover modifications and equivalent arrangements. For example, it is to be understood that this disclosure contemplates that, to the extent possible, one or more features of any embodiment can be combined with one or more features of any other embodiment.

What is claimed is:

1. A syringe system comprising:
    a syringe body comprising a hollow lumen and a distal end comprising a syringe tip, the syringe body being configured to house a plurality of fluids therein;
    a first plunger positioned in the hollow lumen of the syringe body, forming a first seal with an inner wall of the syringe body, and forming a first compartment between the first plunger and the distal end of the syringe;
    a plurality of recesses disposed about the inner wall of the syringe body near the distal end of the syringe body;
    a second plunger positioned proximal to the first plunger in the hollow lumen of the syringe body, forming a second seal with the inner wall of the syringe body, and forming a second compartment between the first plunger and the second plunger; and
    a transfer tube in fluid connection with the second compartment and the syringe tip,
    wherein the first plunger, upon contacting the plurality of recesses, breaks the first seal with the inner wall of the syringe body, causing fluid contents of the second compartment to flow distally into the first compartment.

2. The syringe system of claim 1, wherein the transfer tube comprises a valve in fluid communication with the syringe tip.

3. The syringe system of claim 2, further comprising an outlet port fluidly connected to an outlet of the valve.

4. The syringe system of claim 3, wherein the outlet port is configured to output a fluid from one or more of the first compartment and the second compartment depending on an orientation of the valve.

5. The syringe system of claim 4, wherein the orientation of the valve comprises one of a first opening state to allow fluid flow from the syringe tip to the outlet port, a second opening state to allow fluid flow from the transfer tube to the outlet port, a third opening state to allow fluid flow from both the syringe tip and the transfer tube to the outlet port, and a closed state to block fluid flow from the syringe tip and the transfer tube.

6. The syringe system of claim 1, wherein the plurality of recesses are scalloped or crenelated.

7. The syringe system of claim 1, further comprising a connection piece positioned between the first plunger and the second plunger.

8. The syringe system of claim 7, wherein the connection piece is a filament.

9. The syringe system of claim 1, wherein the syringe body further comprises an open proximal end having a finger guard affixed thereto.

10. The syringe system of claim 1, further comprising a piston connected to the second plunger, wherein the piston is configured to be activated by a thumb piece.

11. A syringe system comprising:
    a syringe body comprising a hollow lumen and a distal end comprising a syringe tip, the syringe body being configured to house a plurality of fluids therein;
    a first plunger positioned in the hollow lumen of the syringe body, forming a first seal with an inner wall of the syringe body, and forming a first compartment between the first plunger and the distal end of the syringe;
    a plurality of recesses disposed about the inner wall of the syringe body near the distal end of the syringe body;
    a second plunger positioned proximal to the first plunger in the hollow lumen of the syringe body, forming a second seal with the inner wall of the syringe body, and forming a second compartment between the first plunger and the second plunger;
    a transfer tube in fluid connection with the second compartment, the transfer tube comprising a valve having an outlet, wherein the valve is in fluid communication with the syringe tip; and
    an outlet port fluidly connected to the outlet of the valve,
    wherein an orientation of the valve comprises one of a first opening state to allow fluid flow from the syringe tip to the outlet port, a second opening state to allow fluid flow from the transfer tube to the outlet port, a third opening state to allow fluid flow from both the syringe tip and the transfer tube to the outlet port, and a closed state to block fluid flow from the syringe tip and the transfer tube, and
    wherein the first plunger, upon contacting the plurality of recesses, breaks the first seal with the inner wall of the syringe body, causing fluid contents of the second compartment to flow distally into the first compartment.

* * * * *

UNITED STATES PATENT AND TRADEMARK OFFICE
CERTIFICATE OF CORRECTION

PATENT NO. : 9,114,215 B2
APPLICATION NO. : 13/802372
DATED : August 25, 2015
INVENTOR(S) : Cowan et al.

It is certified that error appears in the above-identified patent and that said Letters Patent is hereby corrected as shown below:

ON THE TITLE PAGE:
In the Figure, delete Tag "423" and insert Tag -- 523 --, therefor.

IN THE DRAWINGS:
In Fig. 5, Sheet 5 of 9, delete Tag "423" and insert Tag -- 523 --, therefor.

IN THE SPECIFICATION:
In Column 10, Line 12, delete "inner piston 546" and insert -- inner piston 547 --, therefor.
In Column 10, Line 13, delete "outer sleeve 545" and insert -- outer sleeve 546 --, therefor.
In Column 10, Line 24, delete "check valve 521" and insert -- check valve 523 --, therefor.
In Column 10, Line 27, delete "check valve 521" and insert -- check valve 523 --, therefor
In Column 11, Line 32, delete "syringe 105." and insert -- syringe 100. --, therefor.
In Column 11, Line 51, delete "syringe barrel 105," and insert -- syringe body 105, --, therefor.
In Column 12, Lines 17-18, delete "first compartment 220 or the second compartment 235," and insert -- first compartment 560 or the second compartment 265, --, therefor.

Signed and Sealed this
Fifth Day of July, 2016

Michelle K. Lee
*Director of the United States Patent and Trademark Office*